US00PP13729P39

(12) United States Plant Patent
Brown

(10) Patent No.: US PP13,729 P3
(45) Date of Patent: Apr. 15, 2003

(54) HEUCHERA PLANT NAMED 'CRIMSON CURLS'

(76) Inventor: Ray Brown, St. Marychurch Rd., Newton Abbott, South Devon, TQ12 4SW (GB)

( * ) Notice: Subject to any disclaimer, the term of this patent is extended or adjusted under 35 U.S.C. 154(b) by 53 days.

(21) Appl. No.: 09/728,746

(22) Filed: Dec. 2, 2000

(65) Prior Publication Data

US 2002/0069441 P1 Jun. 6, 2002

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Michelle Kizilkaya
(74) *Attorney, Agent, or Firm*—Mark P. Bourgeois

(57) ABSTRACT

A new cultivar of Heuchera named 'Crimson Curls' that is characterized by a dense, clumping habit and dark purple-brown and crimson leaves with densely curled edges, setting 'Crimson Curls' apart from all other existing varieties of Heuchera known to the inventor.

3 Drawing Sheets

BACKGROUND OF THE INVENTION

The present invention relates to a new and distinct cultivar of Coral Bells known botanically as a Heuchera hybrid and hereinafter referred to by the cultivar name 'Crimson Curls'. The new invention arose as one of many unnamed hybrids, from the inventors nursery garden. 'Crimson Curls' was first selected in May 1996 by the inventor in Newton Abbot, United Kingdom from a hybridization bed planted by the inventor in 1993. While some of the Heucheras that were planted in the bed were unnamed, unpatented hybrids developed at Plant World, others included 'Purple Palace' (unpatented), *Heuchera micrantha* (unpatented), *Heuchera cylindrica* (unpatented), and *Heuchera americana* (unpatented). The inventor planted these specimens in an effort to allow open pollination to occur and select Heucheras exhibiting new leaf variants. The inventor suggests that 'Crimson Curls' may have derived its foliage color partially from 'Purple Palace' (unpatented) and the crispy metallic leaf texture from the species *H. micrantha* (unpatented) or possibly *H. americana* (unpatented). However, the exact parents are unknown.

'Crimson Curls' is distinguished by its dense, clumping habit, its densely curled leaves that look like crispy cabbage, and its dark purple-brown and crimson foliage. In England, where the winter temperatures are cool, the foliage of 'Crimson Curls' has been observed to intensify from its purple-brown color to a bright ruby color that glows in the winter sun. However, during the summer data collection in California the leaves remained dark purple-brown and crimson. The closest comparison variety is 'Chocolate Ruffles' (U.S. Plant Pat. No. 8,965). In comparison 'Crimson Curls' forms a dense mounded clump with leaves that exhibit dense curls on their edges, where 'Chocolate Ruffles' (U.S. Plant Pat. No. 8,965) exhibits a habit less dense with foliage that is open and flatter.

The new invention was first asexually propagated in Newton Abbot, United Kingdom by the inventor in 1996. Since that time, under careful observation, successive generations have been determined stable and uniform.

SUMMARY OF THE INVENTION

The new Heuchera plant 'Crimson Curls' can be distinguished from all other known varieties of Heuchera by the following characteristics:

1. Densely curled leaf edges.
2. Dense, mounded, clumping habit.
3. Dark purple-brown and crimson foliage.
4. Observed to intensify in foliage color from purple-brown to bright ruby in England during cool winter temperatures.
5. Erect burgundy stalks of white flowers in summer.

BRIEF DESCRIPTION OF THE DRAWINGS

The accompanying color photographs illustrate the distinguishing traits of the new cultivar. Sheet 1 shows a front view of the entire plant in flower on the left, illustrating the flowers, foliage and dense habit in a garden setting. Both photos on sheet 2 show a close-up view of the densely curled foliage. Sheet 3 is a comparison photo showing 'Crimson Curls' and 'Chocolate Ruffles' (U.S. Plant Pat. No. 8,965) side by side and illustrating the dense habit and densely curled leaf edges of 'Crimson Curls' on the left, as compared to the less dense habit and flatter more open leaves of 'Chocolate Ruffles' (U.S. Plant Pat. No. 8,965) on the right. The plants in the photos are 10 months old and were grown in one gallon containers outdoors. The plants were hand watered and air temperatures ranged from 10 to 23 degrees centigrade. All photographs are taken in the spring and summer using conventional techniques and although foliage colors may appear different from actual colors due to light reflectance, they are as accurate as possible by conventional photography.

BOTANICAL DESCRIPTION OF THE PLANT

The following is a detailed description of the Heuchera cultivar named 'Crimson Curls'. Data was collected during the summer months in Arroyo Grande, Calif. from 10 month old plants grown in one-gallon containers. The plants were grown outdoors and were hand watered. The air temperatures ranged from 10 to 23 degrees centigrade. Phenotypic differences may be observed with variations in environmental, climatic, and cultural conditions, without however, any difference in genotype. Color determinations are in accordance with The Royal Horticultural Society Colour Chart except where general color terms of ordinary dictionary significance are used. The growing requirements are similar to the species and no disease problems have been observed.

Botanical classification: Heuchera 'Crimson Curls'.
Common name: Coral Bells.
Type: Evergreen herbaceous perennial.
Use: Partially shaded borders, in containers as accents or massed as a groundcover.
Parentage: Exact parents unknown. The new invention is a hybrid possibly involving *Heuchera micrantha, cylindrica, micans, sanguinea,* 'Purple Palace' and other unnamed Heurcheras (all of which are unpatented), but the exact parents are unknown. The new plant could also possibly be the result of a natural mutation.
Growth rate: Vigorous.
Habit: Dense and mounded clumps.
Height: 45 cm in height.
Width: 37 cm in width.
Hardiness: Zone 3.
Propagation: Tissue culture or division.
Root system: Vigorous and fibrous.
Soil: Plant in moist well-drained soils.
Light levels: Partial shade preferred, but does well in full sun if kept moist.
Special needs: Remove spent blossoms and cut back old foliage in late winter and early spring.
Time to initiate roots: Approximately 6 weeks from initial cutting to a rooted cutting.
Time to develop to a one-gallon: Approximately 6 to 9 months from a rooted cutting to a one-gallon container.
Branching habit: Rosette.
Seasonal interest: White flowers in summer.
Stem:
- *Base.*—Caudex.
- *Base size.*—3 to 5 cm in diameter.
- *Size* (*main stems*).—3 mm in width by 10 cm in length.
- *Size* (*young stems*).—3 mm in width by 7 cm in length.
- *Shape.*—Cylindrical.
- *Surface.*—Sparsely puberulent with long and short hairs.
- *Color.*—Mature stems 187A. Young stems are a combination of 166A, 166B and 166C.

Foliage:
- *Leaf arrangement.*—Basal leaves tufted, forming dense rosette.
- *Leaf division.*—Palmately lobed.
- *Leaf shape.*—Palmatifid with crisped or crispate surface and edges.
- *Leaf base.*—Sagitate.
- *Leaf tip.*—Rounded with notches.
- *Leaf venation.*—Prominent palmate veining with protruding mid-vein and main veins beneath and depressed above. Small ramiform veins coming off main veins.
- *Vein color* (*upper surface*).—166D.
- *Vein color* (*lower surface*).—166D. Small ramiform veins 187A.
- *Mature leaf surface* (*upper*).—Puberulent with sparse long and short hairs.
- *Mature leaf surface* (*lower*).—Puberulent with sparse long and short hairs.
- *Young leaf surfaces.*—Glossy.
- *Leaf margins.*—Ciliate, bisserate and sinuate. Revolute at tips and involute at sinuses.
- *Measurement of curls per sinus.*—Approximately 6 curls per 4 cm (each lobe, on either side of sinus, is 2 cm) and approximately 5 to 8 folds of leaf edge.
- *Leaf length* (*mature*).—9 cm in length.
- *Leaf width* (*mature*).—11 cm in width.
- *Leaf length* (*young*).—4 cm in length.
- *Leaf width* (*young*).—4 cm in width.
- *Young leaf color* (*upper surface*).—A combination of 166A and 183A, B with iridescent and translucent surface qualities which produce an overlay of 71A and 186A.
- *Young leaf color* (*lower surface*).—183A, B and 187A.
- *Mature leaf color* (*upper surface*).—A combination of 166A and 147A with translucent edges 71A and 187A.
- *Mature leaf color* (*lower surface*).—183A and 187A.
- *Foliar fragrance.*—Slight grass-like scent.

Flower:
- *Type.*—Paniculate.
- *Shape.*—Campanulate.
- *Color.*—White on burgundy stems.
- *Fragrance.*—None observed.
- *Petals.*—Five in number.
- *Petal shape.*—Spatulate-shaped.
- *Petal length.*—2 mm in length.
- *Petal width.*—1 mm in width.
- *Bud color.*—187A.
- *Calyx.*—Five sepals.
- *Sepal color.*—A combination of 187A, 187B, 187C and 187D.
- *Sepal shape.*—Urn-shaped.
- *Blooming period.*—Mid-summer for approximately four weeks.
- *Quantity of flowers.*—25 to 40 per stalk.
- *Bloom stalk.*—53–65 cm in height.
- *Stalk form.*—Erect, lightly leaning and leafy prior to panicle with internodes of 1–5 cm between nodes.
- *Stalk color.*—187A.
- *Panicle size.*—17–23 cm in height and 6–8 cm in width.
- *Seed.*—No seed production observed.

Reproduction organs:
- *Stamens.*—Five, exserted.
- *Pollen color.*—169A.
- *Amount of pollen.*—Moderate.
- *Stigmas.*—Two.
- *Color.*—White.
- *Ovary position.*—Partially inferior.

What is claimed is:

1. A new and distinct variety of Heuchera plant named 'Crimson Curls' as described and illustrated.

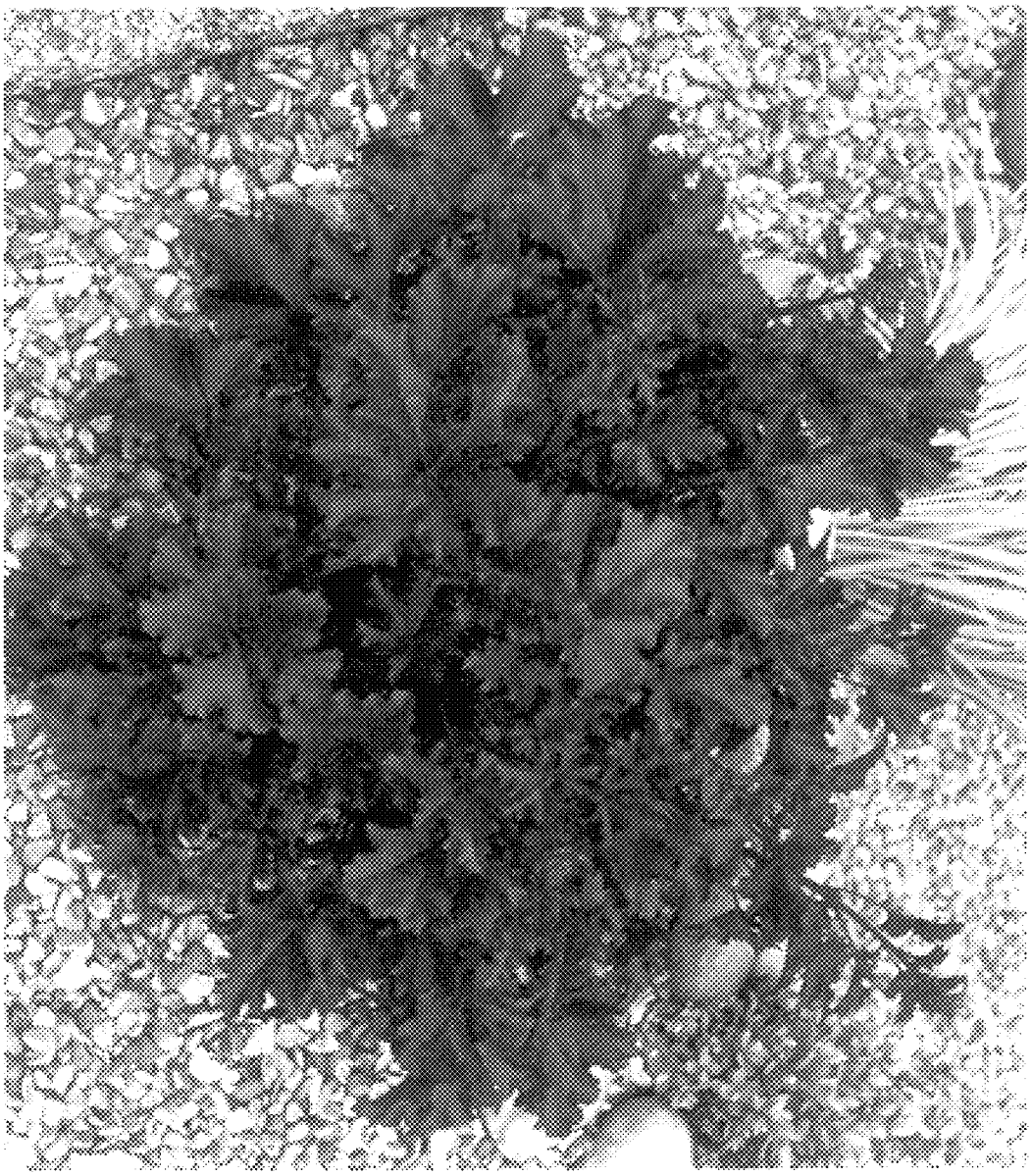

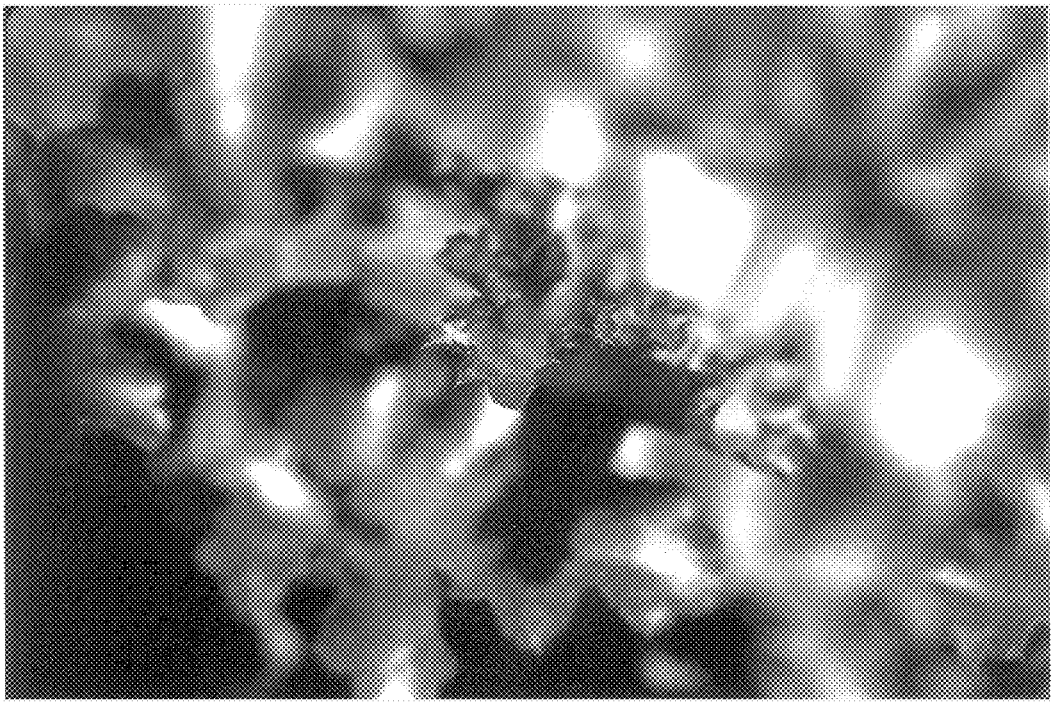
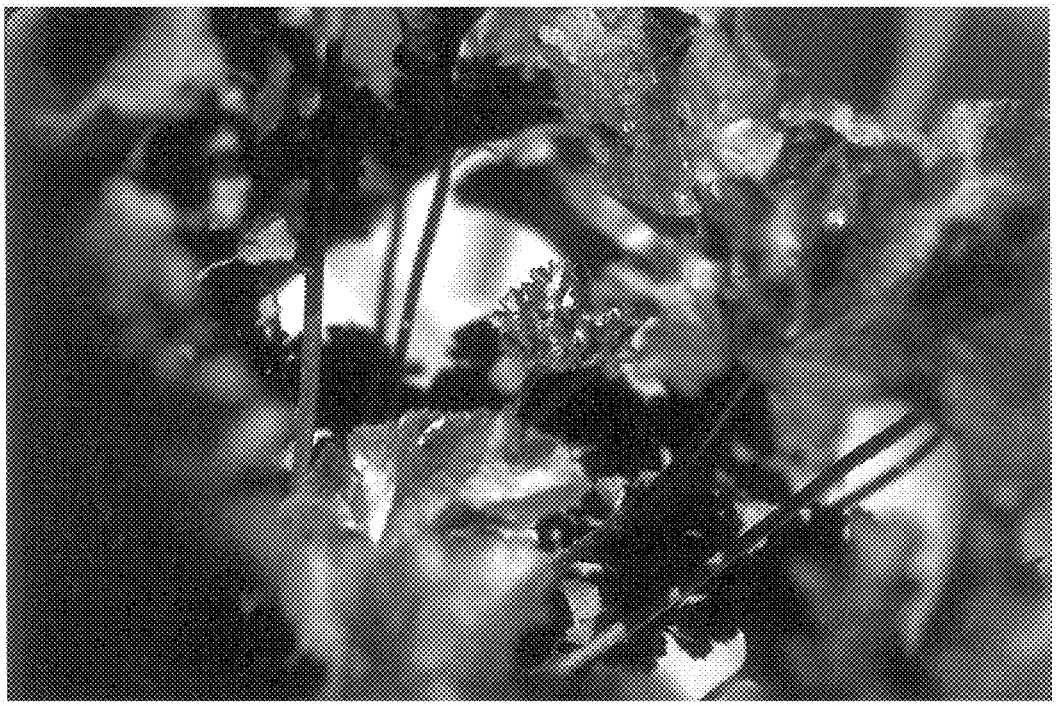

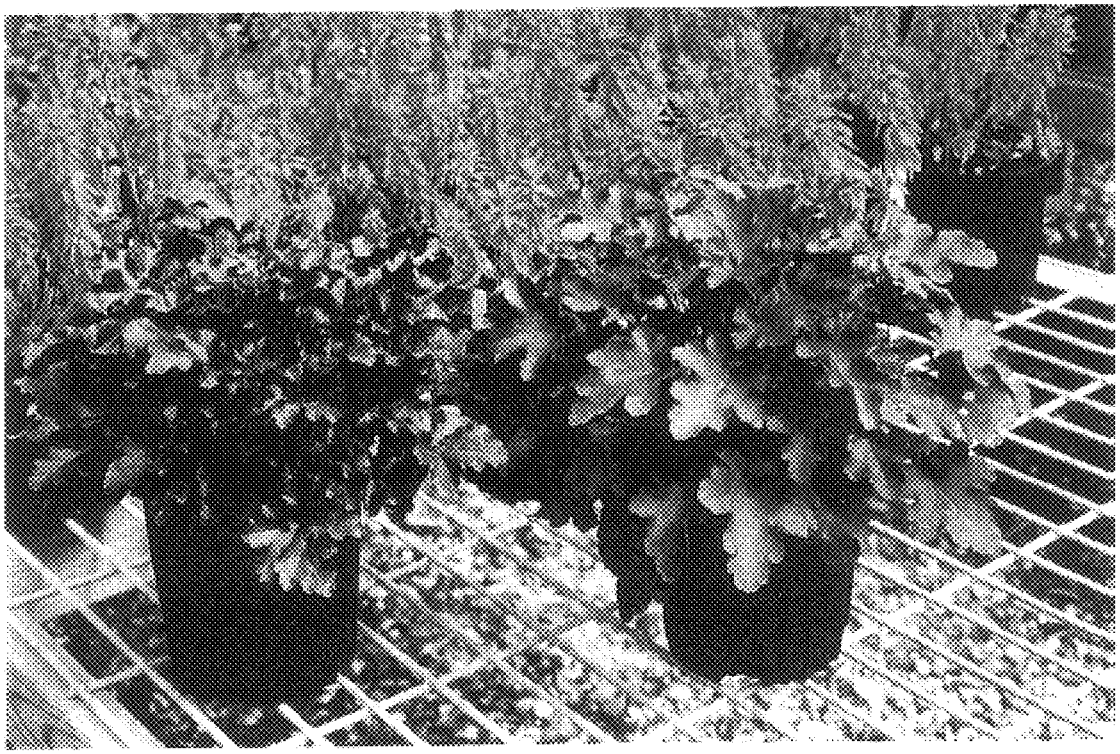

* * * * *